US009138422B2

United States Patent
Huang et al.

(10) Patent No.: US 9,138,422 B2
(45) Date of Patent: Sep. 22, 2015

(54) METHOD OF USING ANTIMYCIN A TO DOWNREGULATE WNT/B-CATENIN PATHWAY TO TREAT GEFITINIB RESISTANT CANCER

(71) Applicants: Chi-Ying F. Huang, Taipei (TW); Chi-Tai Yeh, Taipei (TW); Chun-Hung Wu, Taipei (TW); Yu-Wen Liu, Taipei (TW)

(72) Inventors: Chi-Ying F. Huang, Taipei (TW); Chi-Tai Yeh, Taipei (TW); Chun-Hung Wu, Taipei (TW); Yu-Wen Liu, Taipei (TW)

( * ) Notice: Subject to any disclaimer, the term of this patent is extended or adjusted under 35 U.S.C. 154(b) by 0 days.

(21) Appl. No.: 14/058,066

(22) Filed: Oct. 18, 2013

(65) Prior Publication Data
US 2014/0045841 A1 Feb. 13, 2014

Related U.S. Application Data

(62) Division of application No. 13/158,783, filed on Jun. 13, 2011, now abandoned.

(51) Int. Cl.
*A61K 31/365* (2006.01)
*A61K 31/5377* (2006.01)
*A61K 45/06* (2006.01)
*A61K 31/517* (2006.01)

(52) U.S. Cl.
CPC ............. *A61K 31/365* (2013.01); *A61K 31/517* (2013.01); *A61K 31/5377* (2013.01); *A61K 45/06* (2013.01)

(58) Field of Classification Search
CPC ............ A61K 2300/00; A61K 31/365; A61K 31/517; A61K 31/5377; A61K 45/06
See application file for complete search history.

(56) References Cited

U.S. PATENT DOCUMENTS

2005/0239873 A1* 10/2005 Hockenbery et al. ......... 514/450
2007/0072828 A1*  3/2007 Yoo ................................ 514/60

OTHER PUBLICATIONS

Herbst et al. Gefitinib—a novel targeted approach to treating cancer. Nature Reviews, Cancer. Dec. 2004.*
Moon et al. Wnt and beta-catenin signaling: diseases and therapies. Nature Reviews: Genetics, vol. 5, Sep. 2004.*

* cited by examiner

*Primary Examiner* — Anna Pagonakis
(74) *Attorney, Agent, or Firm* — WPAT, P.C.; Anthony King

(57) ABSTRACT

The present invention provides a method for inhibiting the growth of cancer stem cells, particularly colorectal cancer stem cells, liver cancer stem cells, lung cancer stem cells or breast cancer stem cells, comprising administering to a subject in need thereof a therapeutically effective amount of a compound of antimycin A or a pharmaceutically acceptable salt thereof, together with a pharmaceutically acceptable carrier.

1 Claim, 6 Drawing Sheets

_US 9,138,422 B2_

METHOD OF USING ANTIMYCIN A TO DOWNREGULATE WNT/B-CATENIN PATHWAY TO TREAT GEFITINIB RESISTANT CANCER

FIELD OF THE INVENTION

The present invention relates to a method for inhibiting the growth of cancer stem cells.

BACKGROUND OF THE INVENTION

Cancer stem cells (CSCs)/tumor-initiating cells have been defined as a subset of tumor cells responsible for initiating and sustaining tumor development. It was evidenced that the existence of lung CSCs and their stem cell properties contributed to the tumorigenesis and drug resistance. (Hanahan D and Weinberg R A.; Hallmarks of cancer: the next generation. *Cell*, 144:646-74, 2011.) It was also well known that to regulate carcinogenesis of lung cancer facilitated the search of novel therapeutics which specifically targeted lung cancer stem cells (LCSCs) and/or CSCs of other cancer types. Particularly, this lead to improved efficacy in treatment and even prevention of carcinogenesis of all types of cancers (Chang A; Chemotherapy, chemoresistance and the changing treatment landscape for NSCLC. *Lung Cancer* 71:3-10, 2011.)

It was reported by Nguewa P A et al. that in advanced NSCLC (lung adenocarcinoma) patients with specific EGFR mutations, the treatment outcome of EGFR-TKIs was significantly better than traditional chemotherapy drugs (Nguewa P A et al.; Tyrosine kinase inhibitors with antiangiogenic properties for the treatment of non-small cell lung cancer. *Expert Opin Investig Drugs* 20:61-74, 2011; and Pao W and Chmielecki J; Rational, biologically based treatment of EGFR-mutant non-small-cell lung cancer. *Nat Rev Cancer* 10:760-74, 2010.) However, almost all patients who received EGFR-TKI treatment would eventually develop drug resistance. For instance, the median progression free survival after first-line treatment of gefitinib in sensitive EGFR mutated patients is about 10 months, and only 2.2 months in patients with erlotinib as second line treatment after chemotherapy. The exact mechanism(s) responsible for the development of drug resistance remains unclear, but the existence of CSCs presents a strong argument. There is currently no effective treatment to overcome drug resistance once it has emerged.

SUMMARY OF THE INVENTION

Accordingly, the invention provides a new treatment of a cancer with a compound of formula I (antimycin A).

In one aspect, this subject invention provides a method for inhibiting the growth of cancer stem cells, comprising administering to a subject in need thereof an effective amount of a compound of formula I (antimycin A) or a pharmaceutically acceptable salt thereof.

In another aspect, the present invention relates to a method for inhibiting the growth of cancer stem-like side population (SP) cells comprising a therapeutically effective amount of antimycin A or a pharmaceutically acceptable salt thereof.

In a yet aspect, the present invention provides a method for treating a cancer with a reduced resistance acquired by the administration of an anti-cancer agent, comprising administering to a subject in need thereof a therapeutically effective amount of a compound of formula I (antimycin A) or a pharmaceutically acceptable salt thereof in combination of an administration of an anti-cancer agent.

In a further aspect, the present invention provides a method for treating a cancer comprising administering to a subject in need thereof an anti-cancer agent in combination of a therapeutically effective amount of a compound of formula I (antimycin A) or a pharmaceutically acceptable salt thereof. In one example of the present invention, the method for treating a cancer comprise administration of an anti-cancer agent (e.g. gefitinib), in combination of administration a therapeutically effective amount of a compound of formula I (antimycin A) or a pharmaceutically acceptable salt thereof.

In a further and yet aspect, the present invention provides a method for downregulating Wnt/β-caterin pathway, comprising administering to a subject in need thereof a therapeutically effective amount of a compound of formula I (antimycin A) or a pharmaceutically acceptable salt thereof.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments, which are presently preferred. It should be understood, however, that the invention is not limited to the precise arrangements and instrumentalities shown.

In the drawings.

Figure 6:
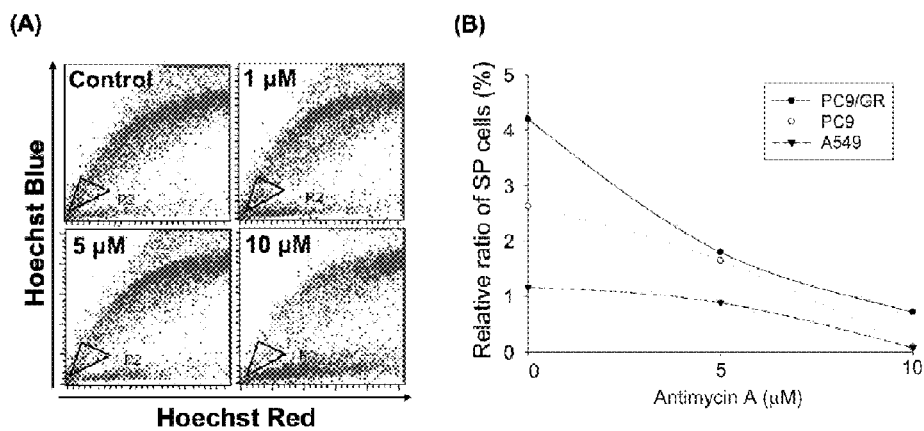

FIG. 6 shows that antimycin A reduced the cell number in the cancer stem-like SP cells. PC9/GR cells were stained with Hoechst 33342 in the presence of the indicated concentrations antimycin A, and then analyzed (A); and the relative ratios of SP cells number of PC9/GR, PC9, and A549 in antimycin A-treated samples were shown by comparing with them with SP cell number in antimycin A-untreated samples (B).

Figure 7:
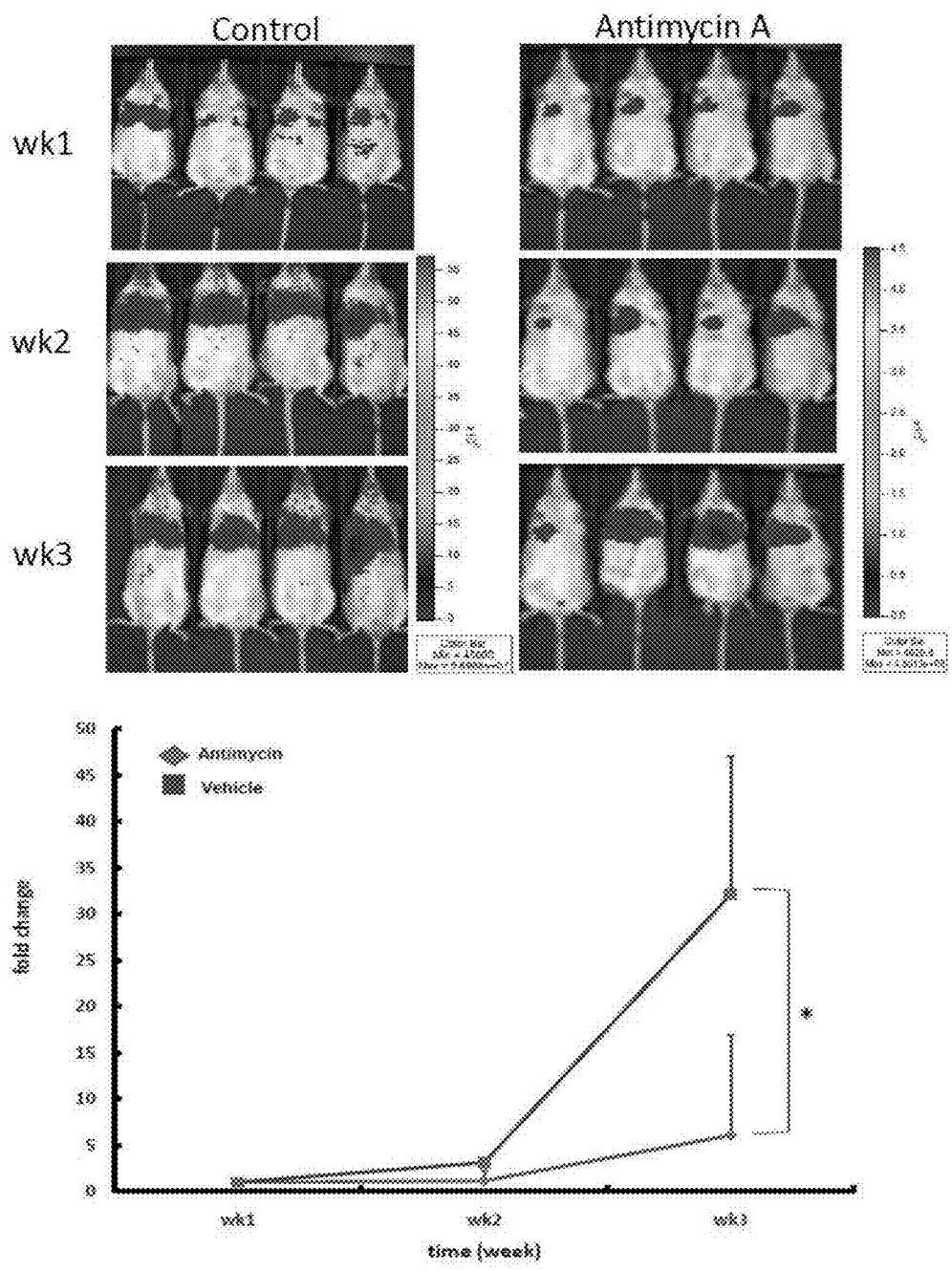

FIG. 7 depicts that the treatment of antimycin A in NOD/SCID mice significantly suppressed A549 tumorigenesis; immune compromised NOD/SCID mice were initially inoculated with A549 Luc cells via tail vein injection; bioluminescence emitted from A549 Luc cells were then quantitatively measured using IVIS spectrum system one week post tumor inoculation; mice exhibiting approximately equal bioluminescence intensity were grouped for experimentation; this procedure was performed to ensure approximately equal tumor burden prior to antimycin A treatment; the entire treatment/monitoring process lasted 3 weeks post tumor inoculation; Antimycin A-treated mice exhibited significantly lower tumor burdens in the lungs when compared with the control animals, as evaluated by the fold change in the bioluminescence intensity of A549 Luc lung tumor cells. By the end of experimental period, tumor burden in the control mice was approximately 6-fold higher than antimycin A-treated counterparts; this in vivo data clearly demonstrated antimycin-A's ability in suppressing lung cancer stem cells.

DETAILED DESCRIPTION OF THE INVENTION

The present invention provides a method for treating or preventing a cancer by inhibiting the growth of cancer stem cells or cancer stem-like side population (SP) cells, such as colorectal cancer, liver cancer, lung cancer or breast cancer.

As used herein, the term "cancer stem cells" refers to the cells found within tumors or hematological cancers that possess characteristics associated with normal stem cells, specifically the ability to give rise to all cell types found in a particular cancer; and the cancer stem cells are therefore tumorigenic (tumor-forming), perhaps in contrast to other non-tumorigenic cancer cells.

The term "cancer stem-like side population cells" or "side population cells" or "SP cells" as used herein refers to a subset of stem cells, which are a sub-population of cancer cells that are distinct from the main population of cancer cells on the basis of the markers employed, and have distinguishing biological characteristics (for example, they may exhibit stem cell-like characteristics) from cancer cells, but the exact nature of this distinction depends on the markers used in identifying the side population.

The compound of formula I, known as antimycin A:

formula I

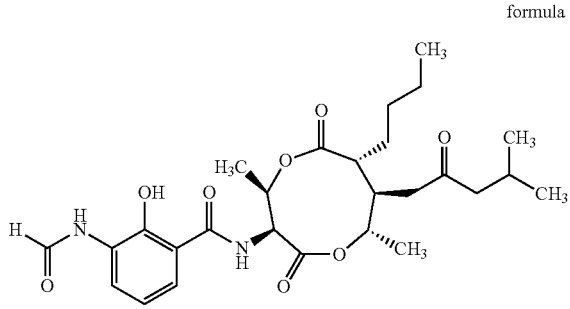

Antimycin A is a chemical compound produced by *Streptomyces* bacteria with a solvent under reflux and purified by silica gel column chromatography afterwards. It can also be prepared by chemical synthesis methods.

The compound of Formula I (antimycin A) was first isolated during the 1940's, and its molecular structure determined a few years later. Antimycin (used to refer to all of the antimycin variants collectively) is an antibiotic that was found to be a potent inhibitor of fungal growth (hence the name), while most bacteria are unaffected. However, due to low content of antimycin A in *Streptomyces* and difficulty in extraction, there has been no further report on antimycin A during the past 15 years.

It is known that antimycin A binds to the Qi site of cytochrome c reductase, thereby inhibits the oxidation of ubiquinol in the electron transport chain of oxidative phosphorylation. The inhibition of this reaction disrupts the formation of the proton gradient across the inner membrane. The production of ATP is subsequently inhibited, as protons are unable to flow through the ATP synthase complex in the absence of a proton gradient. This inhibition also results in the formation of quantities of the toxic free radical superoxide.

As used herein, a "pharmaceutically acceptable salt" refers to a salt that is suitable for administration to a subject to achieve the inhibition of cancer stem cells described herein, without unduly deleterious side effects in light of the severity of cancer and necessity of the treatment. In the example of the invention, antimycin A or a pharmaceutically acceptable salt thereof may be used for inhibiting the growth of cancer stem cells or cancer stem-like side population (SP) cells.

As used herein, the term "pharmaceutically acceptable carrier" refers to any of the standard pharmaceutical carriers such as sterile solutions, tablets, coated tablets, and capsules. Typically such carriers contain excipients such as starch, milk, sugar, certain types of clay, gelatin, stearic acids or salts thereof, magnesium or calcium stearate, talc, vegetable fats or oils, gums, glycols, or other known excipients. Such carriers may also include flavor and color additives or other ingredients. Examples of pharmaceutically acceptable carriers include, but are not limited to, the following: water, saline, buffers, inert, nontoxic solids (e.g., mannitol, talc). Compositions comprising such carriers are formulated by well known conventional methods. Depending on the intended mode of administration and the intended use, the compositions may be in the form of solid, semi-solid, or liquid dosage forms, such, for example, as powders, granules, crystals, liquids, suspensions, liposomes, pastes, creams, salves, etc., and may be in unit-dosage forms suitable for administration of relatively precise dosages.

"A therapeutically effective amount" as used herein refers to an amount necessary to inhibit the growth of cancer stem cells or side population cancer cells. A therapeutically effective amount differs according to the administration route, excipient usage and co-usage of other active agents. In one example of the invention, the therapeutically effective amount of antimycin A is at the concentration of 0.01 to 1000 µM, particularly 0.5 to 50 µM.

By using UV-equipped flow cytometer, it was successfully detected and isolated a small percentage of cancer stem-like side population (SP) cells from several types of lung cancer cell lines, which appear to have characteristics of self renewal, clonogenicity and stemness genes expression. According to the invention, antimycin A was evidenced to have an activity in inhibition of cancer stem cells, including lung cancer cell line—A549 and liver cancer cell line—Huh7. However, the relatively lower cytotoxicity of antimycin A in two non-tumor cells as compared with cancer cell lines. It was found in the present invention that antimycin A had an unexpectedly high activity in inhibiting the formation of primary tumor spheroids through downregulates Wnt/β-catenin pathway and depletes CD133-positive population in lung cancer stem cells. Furthermore, it was found in the present invention that the addition of antimycin A to gefitinib (GR) overcame acquired resistance to gefitinib in PC9 lung adenocarcinoma cell lines. It was also evidenced that the pretreatment of antimycin A in NOD/SCID mice provided a significant efficacy in suppressing A549 tumorigenesis.

In the invention, antimycin A was evidenced to have a high activity in inhibition of the growth of different cancer stem cells, including lung cancer cell line—A549 and liver cancer cell line—Huh7. However, antimycin A had almost no cell toxicity to normal cells including foreskins fibroblast cells and non-tumorigenic breast epithelial cells.

In addition, the present invention provides a method for treating a cancer with a reduced resistance acquired by the administration of an anti-cancer agent, comprising administering to a subject in need thereof a therapeutically effective amount of a compound of formula I (antimycin A) or a pharmaceutically acceptable salt thereof in combination of an administration of an anti-cancer agent. According to the present invention, the compound of formula I may be administered simultaneously or before the anti-cancer agent is administered.

As used herein, the term "anti-cancer agent" refers to any agent that can treat or prevent a cancer or a tumor. In one example of the invention, the anti-cancer agent is gefitinib or erlotinib. Gefitinib or erlotinib is a small-molecule tyrosine kinase inhibitor (TKI) which inhibits EGFR phosphorylation and thus the activation of receptor tyrosine kinase (in the case of lung cancer, EGFR).

It was also evidenced in the present invention that antimycin A provided an efficacy in downregulating Wnt/β-caterin pathway. Wnt/β-caterin pathway also known as Wnt/β-caterin signalling pathway, which a network of β-caterin known for their roles in cancer. Wnt signaling in the dorsal region of the neural tube also controls the expression of a transcription factor Gli3, one of the main inhibitors of the Shh/Gli pathway, and it is by signaling through the Wnt/β-catenin pathway that Wnt is able to activate and control the expression of the Gli3 transcription factor to repress transcriptional activity of Shh/Gli in the dorsal region of the neural tube and elicit dorsal cell fates.

The present invention is further illustrated by the following example, which is provided for the purpose of demonstration rather than limitation.

EXAMPLE 1

Extraction and Isolation of Antimycin A with Testing on the Growth of Human Cancer Cells and Normal Cells Antimycin A, derived from *Streptomyces* sp., is an inhibitor of electron transport chain at mitochondrial complex III. This inhibition results in an elevation in the production of ROS, thereby causing damage to mitochondrial DNA, lipids and proteins, collapse of the mitochondrial membrane potential, which opens up the mitochondrial permeability transition pores, leading to release of pro-apoptotic proteins into the cytoplasm, thereby inducing apoptosis. Therefore, antimycin A is broadly employed to simulate cellular degenerative conditions in vitro.

Figure 1:
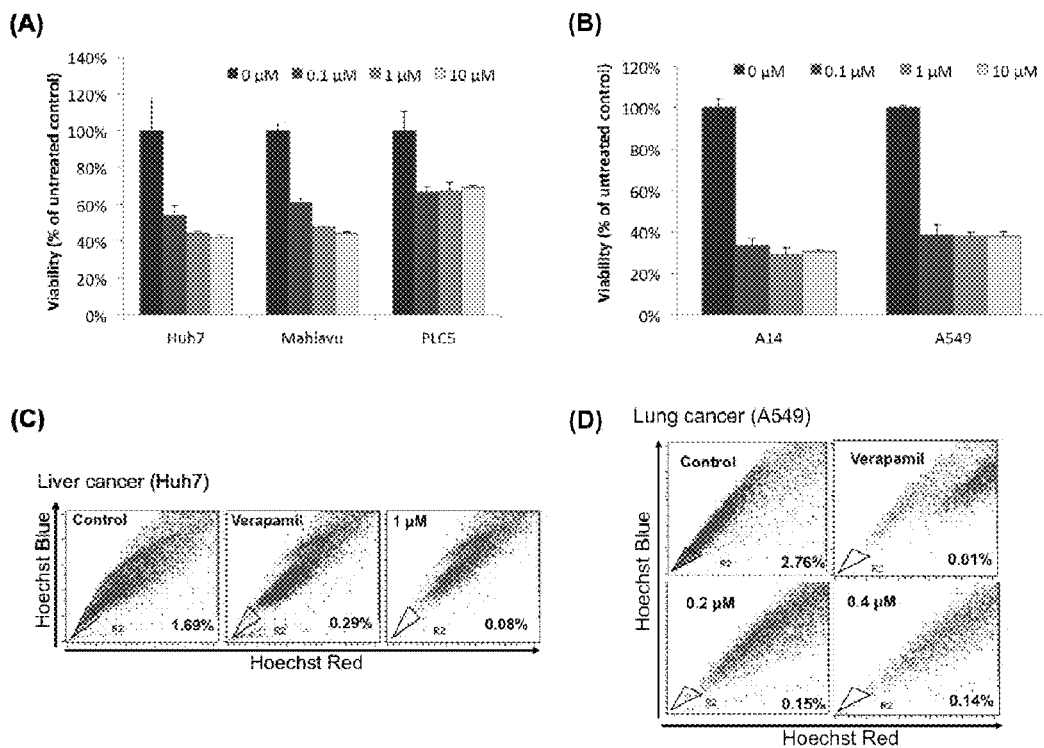
FIG. 1 shows the cytotoxicity of antimycin A in liver (A) and lung cancer cells (B); wherein the cells were incubated with 0, 0.1, 1, 10 μM of antimycin A for 72 hours; and the cell viability was then evaluated by MTT assay; the side populations isolated from Huh7 (liver cancer cell line) (C) and A549 (lung cancer cell line) (D) were significantly decreased after treating with antimycin A.

In the present invention, the anti-proliferative effects of antimycin A were assessed on human cancer cell lines, using the MTT assay, with normal HUVEC and MLF cells as controls. As shown in FIGS. 1 A & B, growth of all of the cancer cells tested was inhibited in a concentration-dependent manner by antimycin A. The estimated $IC_{50}$ determined for antimycin A in these cancer cell lines ranged from 0.6~4.5 µM, particularly in conditions where an antimycin A concentration of 0.6 µM significantly inhibited the A549 cell growth. Interestingly, antimycin A had little anti-proliferative effect on normal HUVEC and MLF cells (see FIGS. 1C & D). Therefore, we tested the effects of antimycin A on liver and lung cancer stem-like SP cells. As shown in FIG. 1 E, antimycin A treatment reduced the Huh7 cells numbers in the SP fraction dose-dependently, the percentage of SP cells was significantly decreased from 1.69% to 0.08% by 1 µM. Similar results were obtained using lung cancer stem-like SP cells (FIG. 1F). The results indicate the antimycin A suppressed Hoechst 33342 export by inhibiting transporters highly expressed on SP cells.

Preparation, Isolation, Culturing and Sorting the Target Cancer Stem Cells

Freezing and thawing cultured cells Remove vial of frozen cells from the nitrogen freezer and transfer to a 37° C. heat block (or the incubator) to thaw (thawing generally takes only 1-2 minutes). Clean outside of tube with alcohol before opening. Although you can spin down the thawed cells, resuspend them, and add thawed cells to ~20 ml of chilled fresh medium.

A549 and PC9 cells were grown in monolayer cell culture and maintained in DMEM medium (supplemented with 10% fetal bovine serum and 1 mM sodium pyruvate) in a humidified atmosphere with 5% CO2 at 37° C. Cells were grown in polystyrene-coated T75 (75 cm$^2$) cell culture flasks, and were harvested in logarithmic phase of growth. The cells were maintained at the above-mentioned culture conditions for all experiments.

To examine the existence of cancer stem cells in hepatocellular carcinoma cancer cell lines, the stem-like side population (SP) cells will be isolated by flow cytometry and cell sorting techniques. SP cells that express ATP-binding cassette (ABC) transporters (ABCG2) and Hoechst 33342 efflux activity will be sorted by FACS Aria III system.

Figure 2:
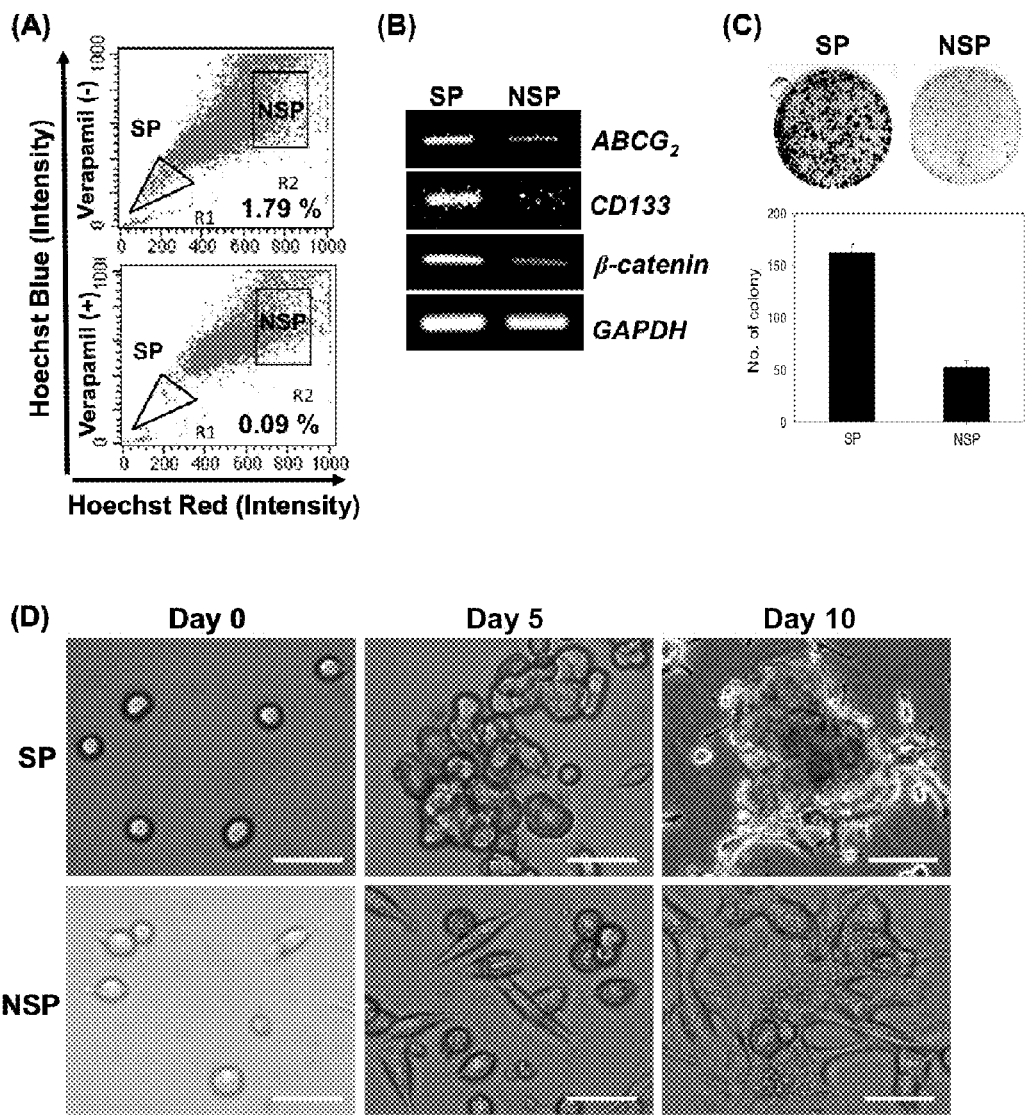
FIG. 2 shows that A549 side population cells possessed higher clonogenicity and expressed stem cell markers; wherein A549 CSCs were sorted using Hoechst 33342 and ABCG2 inhibitor, verapamil, and the R1 gate represents the side population (SP) cells (1.79% of total cells) and the R2 gate represents the NSP (non-SP) cells. Both of them were collected for the subsequent research (A); the RT-PCR assay showed that SP cells contained elevated transcripts of stem cell markers (B); the clonogenic assay showing the clonogenicity of SP cells was markedly higher than that of non-SP cells (C); and the cell morphology of freshly sorted SP and non-SP cells after seeding for 0, 5 and 10 days (D); indicating the morphological differences in both SP (small and round in shape) and non-SP cells (fibroblast-like) were very distinct (scale bar=50 μm).

A549 side population cells possess higher clonogenicity and express stem cell markers. We first identified and isolated side population (SP) cells from A549 lung cancer cell line using Hoechst 33342 DNA binding dye and verapamil (FIG. 2A). The isolated SP cells were cultured for further characterization. It was found that mRNA transcripts used for demonstrating the "stemness" of cancer stem cells namely ABCG2, CD133 and β-catenin were significantly higher in SP cells than that in non-SP counterparts (FIG. 2B). When cultured and assayed for clonogenicity, SP cells exhibited a significantly heightened ability in forming colonies when comparing to non-SP counterparts (FIG. 2C). Importantly, SP cells, when cultured in stem cell medium, appeared to form tumor spheroids while non-SP lacked this ability (FIG. 2D). Collectively, SP cells isolated from A549 lung cancer cell line demonstrated a spectrum of stem cell characteristics described above.

Antimycin A Exposure

Antimycin A was dissolved in DMSO at a concentration of 10 mM and was stored in a dark-colored bottle at −20° C. as a stock solution. The stock was diluted to the required concentration with serum-free medium immediately before use. Before treatment with antimycin A, the medium was removed when cells were about 70% confluent, the cells were starved overnight in serum-free medium and then exposed to antimycin A at different concentrations (0-10 µM) and for different periods of time (0-48 h).

Assessment of the Growth of Lung Cancer Stem Cells Following Antimycin A Treatment MTT dye was used to test the effects of antimycin A on cell growth and viability of lung cancer sphere cells. Antimycin A was dissolved in DMSO at 10 mM as a stock solution before diluting with growth medium to a final DMSO concentration of <0.05%. The cancer cells were seeded into 96 well plates in growth medium at 2000 cells/well. After 16~20 hours cells were treated with antimycin A which was previously diluted to required concentrations with growth medium. The cells were incubated for another 72 hours. Fifty μl of MTT (2 mg/ml) was gently added to each well with subsequent incubation for 2 hour at 37° C. For each well, 180 μl of media was carefully removed to not to disturb cells. And 180 μl DMSO was then added into the well followed by pipetting to completely dissolve the MTT formazan crystals. Plate was read within 30 minutes at absorbance at 570 nm with a reference filter of 660 nm by spectrophotometer.

Figure 3:
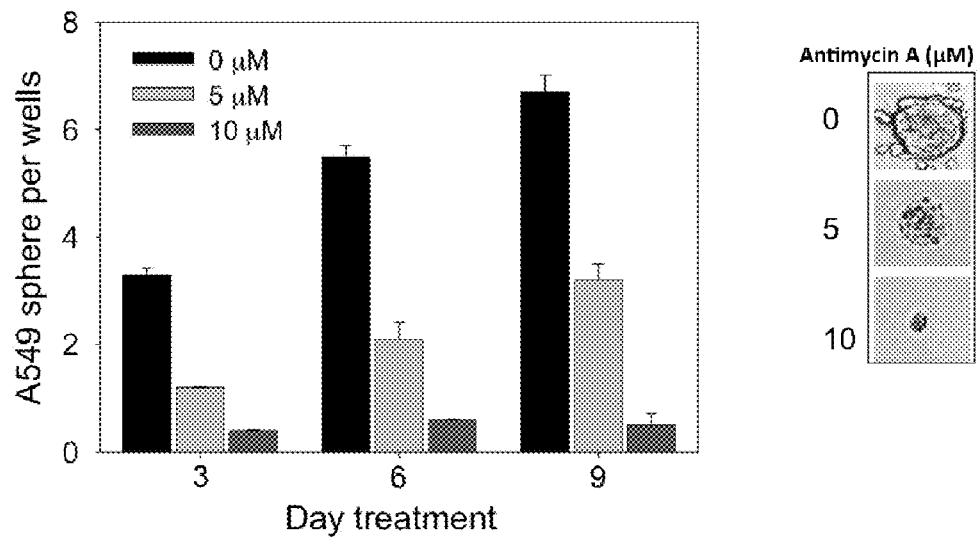
FIG. 3 shows the anti-transforming effect of antimycin A on tumor spheroids; wherein the A549 SP cells were seeded in suspension and treated with antimycin A (0~10 μM) for different incubation time; the micrographs of spheroids formed in suspension were shown in the right panels; at the end of incubation period, all the spheroids were collected and measured by trypan blue assay.

Antimycin A was found to exhibit anti-transforming ability against A549 tumor spheroids. A549 SP cells, seeded in suspension and treated with different concentrations of antimycin A ranging from 0 to 10 μM, exhibited suppressed ability in forming tumor spheroids in a dose-dependent manner (FIG. 3).

Figure 4:
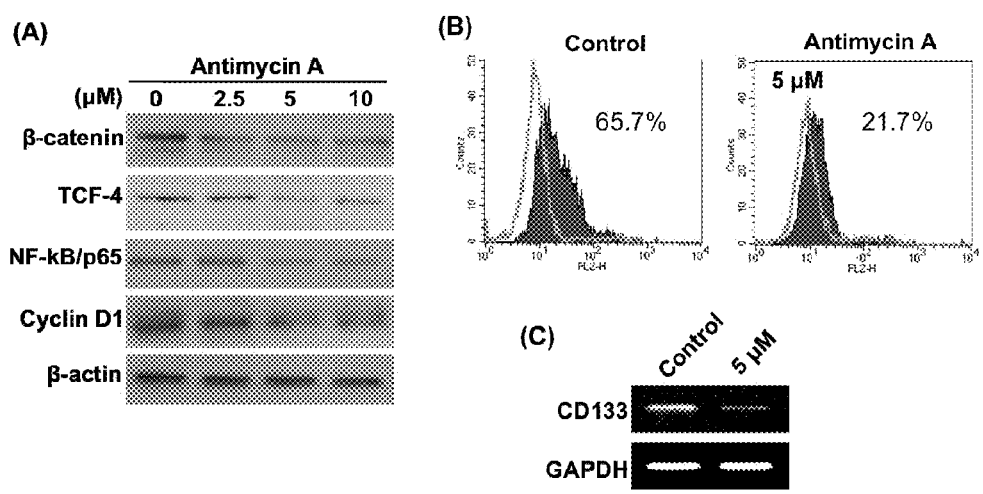
FIG. 4 shows that antimycin A downregulated the Wnt/β-catenin self-renewal pathway and decreased expression of CD133 in A549 SP cells; Antimycin A decreased the protein levels of β-catenin, TCF4, NF-kB/p65 and cyclin D1 in A549 SP cells (A); after antimycin A treatment, FACS analysis revealed that CD133 expression was decreased in A549 SP cells (65.7% to 21.7%) (B) and the RNA level of CD133 was also reduced (C).

The antimycin A mediated its effects on SP cells by disrupting different signalling pathways including β-catenin/TCF-4, NF-κB and cyclin D1 (FIG. 4A). In addition, the antimycin A treatment significantly decreased CD133 expression (from 65.7% down to 21.7%, FIGS. 4B and 4C) in A549 SP cells both on the cell surface and at the transcriptional level.

EXAMPLE 2

Addition of antimycin A to gefitinib (GR) overcomes acquired resistance to gefitinib in PC9 lung adenocarcinoma cell lines.

Figure 5:
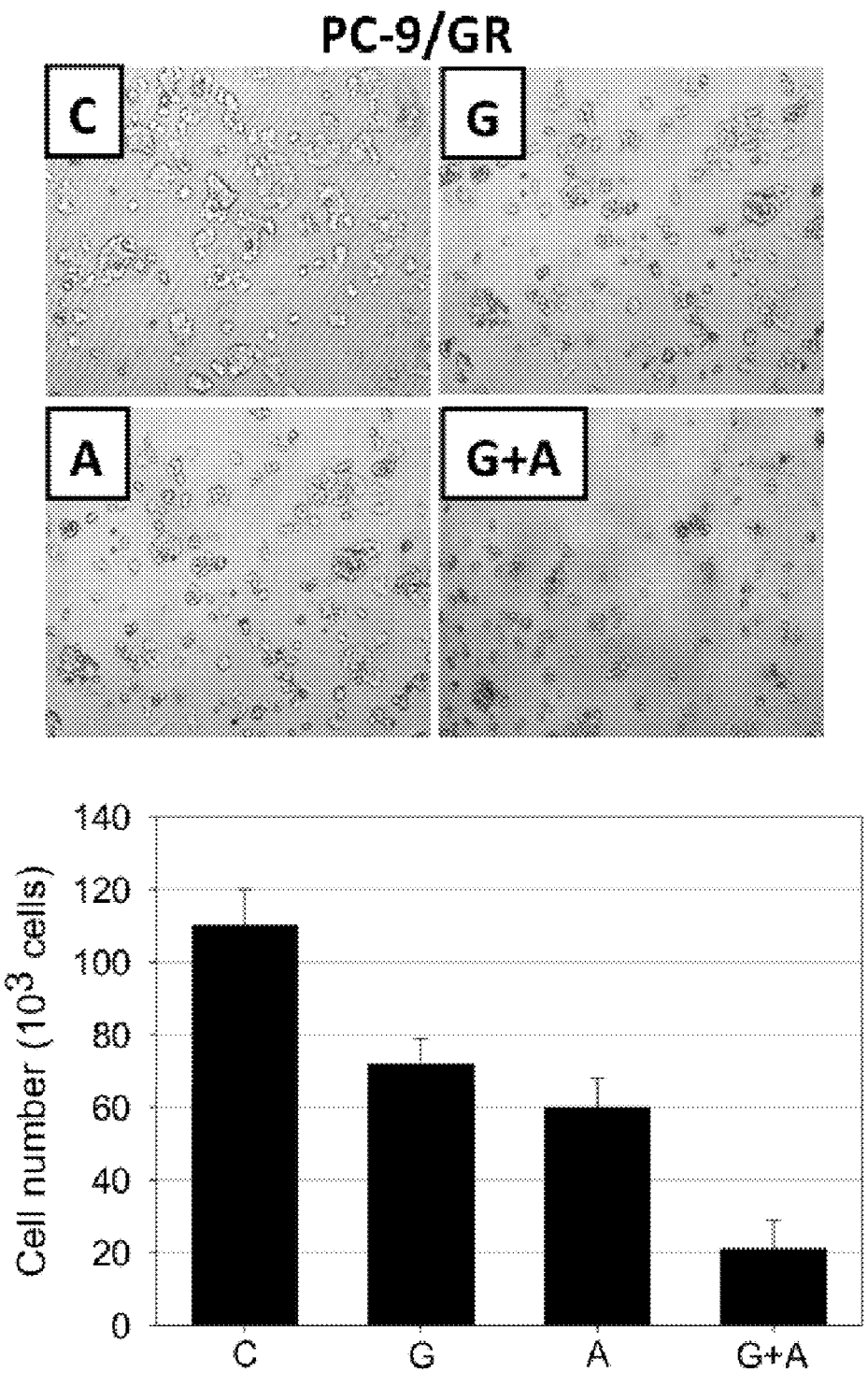
FIG. 5 shows that the addition of antimycin A overcame the acquired resistance to gefitinib in PC9 lung adenocarcinoma cell lines (PC9/GR); wherein PC9/GR cells were grown in Matrigel without or with gefitinib (G) (1 μM), antimycin A (A) (10 μM) or combinations of these drugs (G+A) for 72 hours, and then incubated in drug-free medium. Photographs of the colonies were taken after 2 weeks; the lower graph shows cell numbers from Matrigel experiments; and the cells were harvested by trypsinization and then counted.

PC-9/GR cells were grown in the presence of gefitinib (G), antimycin (A) and both (G+A) drugs. The addition of antimycin A sensitized gefitinib-resistant PC-9 cells towards treatment (FIG. 5). As demonstrated by the micrographs taken from different treatment groups, group with both drugs (A+G) appeared to contain the least number of colonies as compared to the control (C), gefitinib only (G) and antimycin A only (A). The quantitative data were represented in bar graph (lower panel, FIG. 5). The data indicated that antimycin A could overcome gefitinib resistance effectively.

Antimycin A Reduced the Cell Number in the Cancer Stem-Like SP Cells

To further demonstrate antimycin A's ability in overcoming drug resistance, PC-9/GR (gefitinib-resistant PC-9 cells) were subjected to SP analysis. PC-9/GR cells contained approximately 4.3% SP cells. When treated with antimycin A (5 and 10 μM), the percentage of SP cells significantly decreased, indicating antimycin A could overcome gefitinib resistance (FIG. 6). SP cells from other cell lines including PC9 and A549 were also examined and similar results were obtained.

Pretreatment of Antimycin A in NOD/SCID Mice Significantly Suppresses A549 Tumorigenesis Tumor initiating ability is one of the most important hallmarks of cancer stem cells. Therefore, it was further explored the anti-cancer stem cell ability of antimycin A using immune compromised mouse xenograft model. A549-Luc cells were intravenously injected into NOD/SCDI mice and allowed for tumor to develop. One week post injection, lung tumor burden was quantitatively measured and sorted based on the bioluminescence intensity. Mice exhibited approximately equal bioluminescence intensity were grouped. The animals were divided into two groups, one receiving i.p injection of antimycin A and the other with vehicle control. The bioluminescence intensity of the lung tumor burden was monitored on weekly basis. Antimycin A treatment appeared to suppress tumor growth as compared to the vehicle control group (FIG. 7 bottom panels). Tumor burden changes were represented by the fold change in bioluminescence intensity (FIG. 7 upper panel). This data indicated that antimycin A reduced tumor initiating ability of A549 cells in vivo.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method for treating a subject with a lung cancer resistant to gefitinib through downregulating Wnt/β catenin pathway, comprising administering to said subject a therapeutically effective amount of a compound of formula I (antimycin A) or a pharmaceutically acceptable salt thereof in combination with gefitinib,

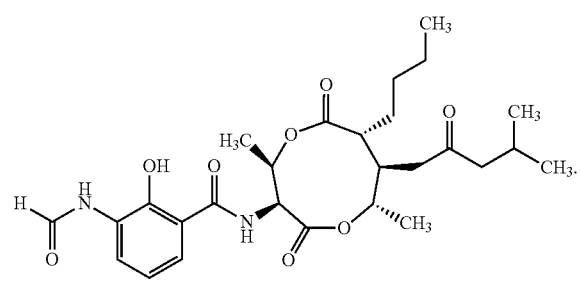

formula I

* * * * *